United States Patent [19]
Adkins, Jr.

[11] Patent Number: 6,112,900
[45] Date of Patent: Sep. 5, 2000

[54] CARE KIT FOR CONTACT LENS WEARERS

[75] Inventor: Nat G. Adkins, Jr., Rosenberg, Tex.

[73] Assignee: Ocusoft, Inc., Richmond, Tex.

[21] Appl. No.: 09/108,593

[22] Filed: Jul. 1, 1998

[51] Int. Cl.⁷ .............................. B65D 69/00; A45C 11/04
[52] U.S. Cl. ......................... 206/570; 206/232; 206/5.1; 514/398; 514/840
[58] Field of Search ..................... 206/581, 570, 206/232, 5.1, 823, 438, 223; 514/157, 398, 235.8, 839, 840; 424/78.04, 78.05; 510/136, 137

[56] References Cited

U.S. PATENT DOCUMENTS

| | | | |
|---|---|---|---|
| 4,347,238 | 8/1982 | Hollingsbee ............................ | 514/157 |
| 4,775,424 | 10/1988 | Wisotki et al. . | |
| 4,780,152 | 10/1988 | Itagaki et al. . | |
| 4,904,698 | 2/1990 | Adkins, Jr. et al. . | |
| 4,957,918 | 9/1990 | Martin et al. ............................ | 514/398 |
| 5,139,705 | 8/1992 | Wittpenn, Jr. et al. ................. | 510/137 |
| 5,456,361 | 10/1995 | Walsh et al. ............................ | 206/570 |
| 5,598,919 | 2/1997 | Taylor . | |
| 5,605,667 | 2/1997 | Powell, Jr. . | |
| 5,614,545 | 3/1997 | Martin et al. ........................... | 514/398 |
| 5,702,379 | 12/1997 | Preiss . | |
| 5,706,935 | 1/1998 | Lorton ........................................ | 206/5 |
| 5,803,244 | 9/1998 | Shefler et al. ............................... | 206/5 |
| 5,881,867 | 3/1999 | Tohill, Jr. et al. ....................... | 206/5.1 |

*Primary Examiner*—Paul T. Sewell
*Assistant Examiner*—Luan K. Bui
*Attorney, Agent, or Firm*—Jo Katherine D'Ambrosio

[57] ABSTRACT

A care kit for reducing irritation and other ocular problems associated with wearing contact lenses is disclosed. The care kit includes at least one solution for the care of contact lenses; at least one non-irritating solution for cleansing eyelids; instructions for informing contact lens wearers of the proper care of contacts in conjunction with eyelid hygiene for improved comfort while wearing contact lenses; and housing for securing the solution for the care of contact lenses, the solution for cleansing eyelids and the instructions. Preferably, the solution for the care of contact lenses can be selected from a group comprising contact lens cleansing solution, disinfecting solution, soaking solution, wetting solution, storage solution, rinsing solution or a combination thereof. The eyelid cleanser can be soaked into a disposable pad and wrapped within an impervious wrapper. Alternatively, the eyelid cleanser is enclosed within an impervious bottle. Instructions to explain the use of contact lens solutions in conjunction with the eyelid cleanser for improved comfort while wearing lenses are included with the kit. In the method of this invention, the eyelid cleanser and contact lens solutions are applied according to the instructions provided.

5 Claims, 2 Drawing Sheets

CARE KIT FOR CONTACT LENS WEARERS

FIELD OF THE INVENTION

The present invention relates to eye care kits. More specifically, it relates to an eye-care kit for facilitating reduced irritation associated with wearing contact lenses.

BACKGROUND OF THE INVENTION

Ocular health refers to eyes as well as structures associated with the eyes, eyelids for example. The eyelids are important in over-all ocular health because they protect the eyes from dangers such as approaching objects or from airborne contaminants, namely pollen, dust particles or other foreign bodies. When an individual blinks, tears are distributed across the cornea to lubricate the surface of the eye. This blinking action also "flushes" foreign materials from the eye.

The eyelids, however, are subject to certain problems, which while very common, are non-the-less bothersome, especially for contact lens wearers, and may lead to other more serious complications. One complication is blepharitis. Blepharitis is a common chronic inflammation of the eyelids characterized by a scaly crust on the lid margins. The condition may be caused by a bacterial infection, or it may be allergic in origin or associated with seborrhea of the face and scalp. Treatment usually involves cleansing the eyelids on a regular basis.

Often associated with or secondary to blepharitis is a bacterial infection of the surface of the skin at the edge of the lid know as an external hordeolum, or of the meibomian glands, either, commonly referred to as styes. Such conditions are accompanied by pain, redness and tenderness of the lid margins. Although styes are often recurring, such conditions can be minimized by regular cleansing of the eyelid margins. A second problem is a chalazion which results from a blockage of one or more of the small oil-producing glands (meibomian glands) found in the upper and lower eyelids. These glands secrete oil which can accumulate on the eyelid and (without proper cleansing) lead to infection where the eyelid becomes swollen, inflamed and painful.

With any of the above-described problems, contact lens wearers must cease wearing their contact lenses and begin treatment. Caught early, proper eyelid hygiene with the use of an eyelid cleanser may minimize the severity of the outbreak, or prevent the problem altogether.

Dry Eye Syndrome refers to a deficiency in the quality and quantity of the tears. As we age, there is a loss of tear production. Quality of tears refers to changes in the tear structure itself with various components "breaking down". It is believed that some of the problems occurring with loss of tear quality may, in fact, be related to eyelid disease. Oil, material and debris on the eyelids may "migrate" into the tear film and contribute to eye irritation and even "build-up" on contact lenses. Build-up refers to deposits which "buildup" on contact lenses and lead to blurring of vision and eye irritation.

Dry Eye Syndrome is also a common problem leading to contact lens drop-outs. Drop-outs refers to lost patients due to discontinuance of lens wear. This problem is particularly acute when the wearer experiences lens discomfort. When the benefit associated with wearing the lens (visual acuity, comfort, etc.) is off-set to a greater degree by discomfort and time-consumption associated with lens care—the patient drops out. The discomfort that causes many individuals to discontinue wearing contact lenses may stem from poor ocular care at the outset of contact lens wear.

An eyelid cleansing composition is taught by U.S. Pat. No. 4,904,698 to Adkins, Jr. et al, incorporated herein by reference in its entirely. A two-component disinfecting and cleaning system for contact lenses is disclosed in U.S. Pat. No. 4,775,424 to Wisotski et al. U.S. Pat. No. 5,598,919 to Taylor discloses a contact lens pouch equipped with a resealable top and prefilled with a contact lens care solution that can be used to clear, disinfect, rinse and store contact lenses once and then be discarded.

None of the above described devices, taken either singlely or in combination, is seen to describe the instant invention as claimed. What is needed and desirable is a system of eye care that provides the necessary products and instructions for cleansing eyelids along with the wearer's routine contact lens care.

SUMMARY OF THE INVENTION

The present invention provides a care kit for reducing irritation and other ocular problems associated with wearing contact lenses. The care kit for contact lens wearers provides the products and instructions for proper use of eyelid cleansers in conjunction with contact lens solutions. A preferred care kit comprises at least one solution for the care of contact lenses; at least one nonirritating solution for cleansing eyelids; instructions for informing contact lens wearers of the proper care of contacts in conjunction with eyelid hygiene for improved comfort while wearing contact lenses; and housing for securing the solution for the care of contact lenses, the solution for cleansing eyelids and the instructions.

Preferably, the solution for the care of contact lenses can be selected from a group comprising contact lens cleansing solution, disinfecting solution, soaking solution, wetting solution, storage solution, rinsing solution or a combination thereof. The eyelid cleanser can comprise an anionic surfactant, a non-ionic thickener and emollient, an amphoteric surfactant, a polyoxyethylenesorbitan fatty acid ester, lauroamphocarboxy glycinate, sodium laureth-13 carboxylate, PEG-15 tallow polyamine, sodium chloride, and at least one microbiological preservative. In a preferred embodiment, the eyelid cleanser comprises a surfactant mixture comprising PEG-80 sorbitan laurate, sodium trideceth sulphate, PEG-150 distearate, cocamidopropylhydroxy sultaine, lauroamphocarboxy glycinate, and sodium laureth-13 carboxylate, the surfactant mixture present in a concentration of 7–10%; PEG-15 tallow polyamine present in a concentration of 0.1–0.5%; sodium chloride present in a concentration of 0.6–0.9%, at least one microbiological preservative selected from the group consisting of Quaternium-15 and benzyl alcohol present in concentration of 0.1–0.5% and a chelating agent present in a concentration of 0–0.1%.

In one preferred embodiment of the present invention, the solution for cleansing eyelids and the solution for the care of contact lenses are in separate receptacles within the housing. In another embodiment, the solution for cleansing eyelids is soaked into a disposable pad and enclosed within an impervious wrapper. Alternatively, the solution for cleansing eyelids is enclosed within an impervious bottle. The instructions can comprise start up instructions for introducing new wearers to the importance of eyelid hygiene in conjunction with proper contact lens care, or, for experienced wearers, the instructions can comprise maintenance instructions regarding the importance of eyelid hygiene in conjunction with proper contact lens care. In one embodiment of the care kit, the instructions are printed on the housing. Alternatively, the instructions are printed within a manual enclosed within the housing.

In a preferred embodiment of the care kit for facilitating reduced irritation associated with wearing contact lenses, the kit comprises: at least one contact lens solution selected from a group comprising cleansing solution, disinfecting solution, soaking solution, wetting solution, storage solution, rinsing solution or a combination thereof; at least one eyelid cleanser comprising a non-irritating fluid cleanser enclosed within an impervious receptacle; instructions for informing contact lens wearers of the proper care of contacts and proper eyelid hygiene for improved comfort while wearing contact lenses when using both the contact lens solution and the eyelid cleanser prior to insertion of lenses and after the removal of lenses; and housing for securing the solution for the care of contact lenses, the solution for cleansing eyelids and the instructions.

An alternative embodiment of a care kit for contact lens wearers comprises: at least one component for eye care and at least one component for eyelid care, the eye care components comprising at least one contact lens solution selected from a group comprising cleansing solution, disinfecting solution, soaking solution, wetting solution, storage solution, rinsing solution or a combination thereof; at least one eyelid cleanser for reducing irritation or the potential for infection of eyelids, the cleanser comprising a non-irritating, antimicrobial fluid soaked into a disposable pad and enclosed within an impervious wrapper; instructions for proper use of the contact lens solution in conjunction with the eyelid cleanser for improved comfort of the wearer, and housing for securing the contact lens solution, the eyelid cleanser and the instructions.

In one preferred method of caring for eyes and eyelids using a care kit for contact lens wearers comprising at least one contact lens solution, at least one eyelid cleanser and instructions for use of both the contact lens solution and eyelid cleanser for improved comfort of wearer, the solution, the cleanser and the instructions secured in a housing; the method comprises: using eyelid cleanser according to instructions for the removal and insertion of contact lenses; and applying contact lens solutions according to instructions for the removal and insertion of contact lenses.

In this method, the contact lens solution is preferably selected from a group comprising cleansing solution, disinfecting solution, soaking solution, wetting solution, storage solution, rinsing solution or a combination thereof. In this preferred method, the eyelid cleanser can comprise an anionic surfactant, a non-ionic thickener and emollient, an amphoteric surfactant, a polyoxyethylenesorbitan fatty acid ester, lauroamphocarboxy glycinate, sodium laureth-13 carboxylate, PEG-15 tallow polyamine, sodium chloride, and at least one microbiological preservative.

DETAILED DESCRIPTION OF THE INVENTION

The present invention is an eye care kit for facilitating reduced irritation associated with wearing contact lenses. This invention addresses the need for a self-contained care kit for contact lens wearers that provides the necessary products and instructions for cleansing eyelids along with the wearer's routine contact lens care. The kit comprises both instructions and solutions which allow the wearer to properly care for contact lenses and the ocular area before inserting or removing the contact lenses. Combined use of the components that comprise the kit of this invention can reduce irritation and diseases of the ocular area thereby increasing the comfort of the contact lens wearer.

Figure 1:
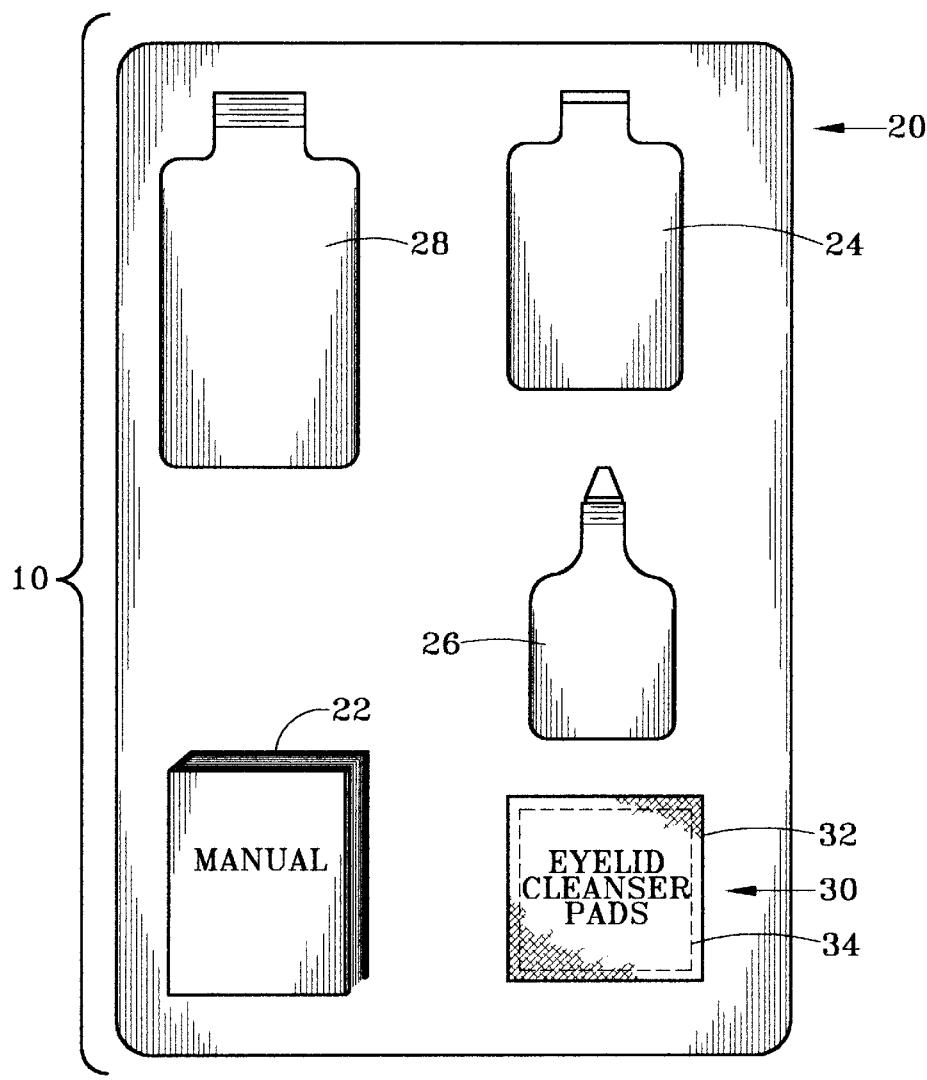
FIG. 1 is a schematic view of the one embodiment of this invention.
Figure 2:
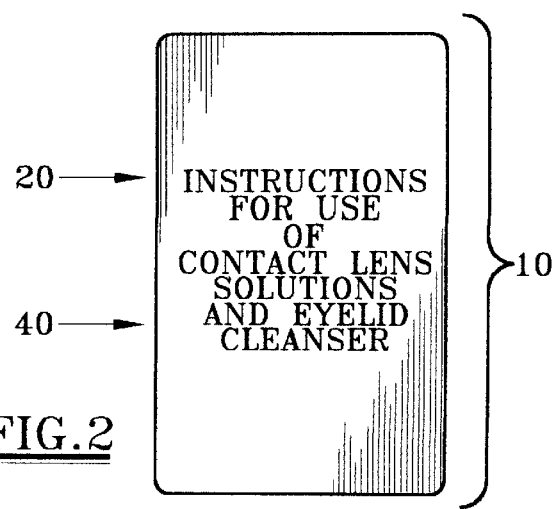
FIG. 2 illustrates another embodiment of the housing of this invention.
Figure 3:
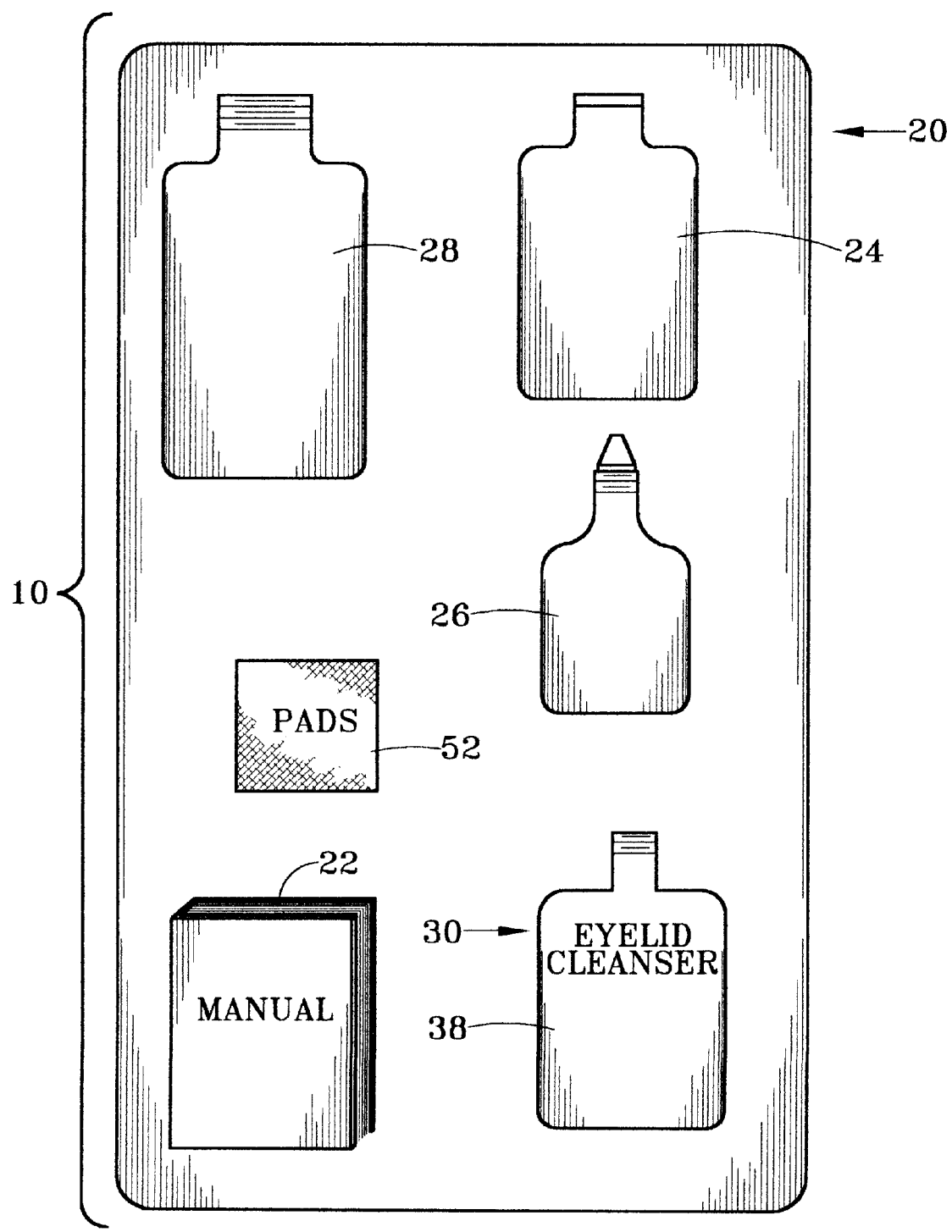
FIG. 3 is a schematic view of an embodiment of the various components that comprise this invention.

FIG. 1 refers to one embodiment of the kit 10 of this invention. The preferred kit 10 comprises a housing 20 for securing the other components of the kit. The other components of the kit can comprise: one or more solutions for the care of contact lenses 24, 26, 28, at least one non-irritating solution for cleansing eyelids 30, and instructions 22, 40 for informing contact lens wearers of the proper eyelid hygiene in conjunction with care of contact lenses for improved comfort while wearing the contact lenses. Additional components related to contact lens care such as a disposable contact lens case (not shown) or an eye lubricant (not shown) can be included within the kit 10. Preferably, the housing 20 and other components 24, 26, 28, 22, 30 are sized so that the components 24, 26, 28, 22, 30 are secured snugly within the housing 20 thereby preventing unnecessary movement or shifting of the various components 24, 26, 28, 22, 30. In one embodiment, the housing 20 is a box as shown in FIGS. 1, 2 and 3. Preferably such housing is a cardboard carton. The components 24, 26, 28, 22, 30 of the kit can be secured within other types of housing 20 or containers without departing from the spirit of the invention, a plastic bubble container unit, for example. In a preferred kit 10, the housing 20 and components 24, 26, 28, 22, 30 within the housing can be sized for the convenience of the user.

The kit 10 can be sized as a travel kit, a starter kit or a care maintenance kit. Both the travel kit and starter kit comprise a housing 20 and components 24, 26, 28, 22, 30 sized to be conveniently transportable within pockets, handbags, briefcases, suit cases or the like. The starter kit can be distributed to new patients, without cost to the patient, to orient them to the proper care of eyelids in conjunction with the care of contact lenses. The care maintenance kit can contain larger units of the solutions 24, 26, 28 and eyelid cleanser 30 for continued use at home.

A preferred size of the housing 20 suitable for the travel kit or starter kit is within a range of about 3¼ inches to about 3¾ inches in height, about 3 inches to about 3¼ inches in width and about 1½ inches to 1¾ inches in depth. More preferably, the housing 20 suitable for the travel kit or starter kit is 3⅝ inches in height, 3⅛ inches in width and 1¹¹⁄₁₆ inches in depth. The components 24, 26, 28, 22, 30 of the travel and starter kits are sized to fit snugly within the housing 20. The contact lens solutions 24, 26, 28 are contained in receptacles sized for travel or starter kits and can hold amounts of solutions within a range of about ¼ ounce to about 1 ounce. The eyelid cleanser 30 is also sized to fit within the travel kit or starter kit, either soaked in a pad within an impervious wrapper 32 as shown in FIG. 1 or, alternatively, in a bottle 38 as illustrated in FIG. 3. The preferred size of the pad is about 2 inches to about 3 inches in width and about 2.5 inches to about 3.5 inches in length. More preferably, the pad is 2.25 inches in width and 3 inches in length. Preferably, the bottle is sized to hold about 0.5 ounces to about 4 ounces. A bottle sized to hold one ounce is preferred. The size of either the wrapped pad 32 or the bottle 38 holding the eyelid cleanser 30 can vary without departing from the spirit of the invention 10.

The care maintenance kit can have housing 20 suitable for holding the larger receptacles of contact lens solutions 24, 26, 28 and eyelid cleansers 32, 38. A preferred size of the housing 20 suitable for the care maintenance kit is within a range of about 5 inches to about 6 inches in height, about 3 inches to about 5 inches in width and about 1 inch to 2½ inches in depth. More preferably, the housing 20 suitable for the care maintenance kit is 5⅛ inches in height, 4 inches in width and 2 inches in depth. The components 24, 26, 28, 22, Ad 30 of the care maintenance kit are also sized to fit snugly within the housing 20. The contact lens solutions 24, 26, 28 are contained in receptacles sized for care maintenance kits; these receptacles can hold amounts of solutions within a range of about 1 ounce to about 16 ounces. The eyelid cleanser 30 is also sized to fit within the care maintenance kit, either soaked in a pad within an impervious wrapper 32 as shown in FIG. 1 or, alternatively, in a bottle 38 as illustrated in FIG. 3. The preferred size of the pad is about 2 inches to about 3inches in width and about 2.5 inches to about 3.5 inches in length. More preferably, the pad is 2.25 inches in width and 3 inches in length. Preferably, the bottle is sized to hold about 0.5 ounces to about 4 ounces. A bottle sized to hold one ounce is preferred.. The sizes of the components 24, 26, 28, 22, 30 within the eye care kit 10 as well as the size of the housing 20 can vary without departing from the spirit of the invention and depend on convenience of shipping and storing as well as convenience of use by the contact lens wearer.

As illustrated in FIGS. 1 and 3, the components within the housing 20 can comprise one or more contact lens solutions 24, 26, 28, an eyelid cleanser 30 and instructional means 22, 40. The contact lens solutions 24, 26, 28 included in the kit 10 of this invention comprise known contact lens products, for example: contact lens cleansing solutions, disinfecting solutions, soaking solutions, wetting and rewetting solutions, storage solutions, rinsing solutions or combinations thereof. A preferred solution is a single solution that cleans, disinfects and stores lenses. Such a cleaning-disinfecting-storage solution sold for use with gas permeable or hard contact lenses is available under the tradename of OPTIMUM, manufactured by Lobob Laboratories, Inc. Other solutions for cleaning, disinfecting, soaking, rinsing, storing or wetting all forms of contact lenses including soft, hard or disposable, are well know in the contact lens industry.

Contact lenses become soiled during wear. Preferably, one or more cleaning solutions are included in the kit 10 and used to remove deposits on the lenses such as cosmetics, oils, lipids, proteins and normal eye secretions. The deposits must be removed to improve the comfort and clarity of the lenses. Contact lenses can be contaminated by bacteria and molds. Disinfectants should be used to prevent eye irritations and disease and are, therefore, included as one of the preferred contact lens solutions in the kit 10 of this invention. Rinsing solutions can be a component of the eye care kit 10 and are used to physically remove foreign deposits on contact lenses. Contact lenses must be hydrated before insertion in the eye to avoid serious pain and discomfort. A preferred eye care kit 10 comprises wetting solutions to rehydrate the lenses either before insertion or used as rewetting drops while the contacts are on the eye. Some wetting solutions may also serve as rinsing solutions for some lens care processes. As discussed supra, some solutions serve multiple purposes, such as the cleaning-disinfectant-storage solution described above. These multiple purpose solutions are well known in the art. A preferred eye care kit 10 comprises the eyelid cleanser 30 and the following contact lens solutions: a cleaning-disinfecting-storage solution, an extra strength cleaner for stubborn surface deposits and a wetting/rewetting solution. Another preferred kit 10 can also comprise a contact lens storage case.

FIG. 1 illustrates one embodiment of a preferred eyelid cleanser 30. A preferred eyelid cleanser 30 is an aqueous solution containing as a major ingredient about 7–10% by weight of the surfactant composition marketed under the tradename Maranol MS-2 by Maranol Chemical Company of Dayton, N.J. Miranol Ms-2, the major ingredient in the composition of the eyelid cleanser is a combination of surfactants including an anionic surfactant, a nonionic thickener, an emollient and an amphoteric surfactant. Preferably, the combination of surfactants comprise PEG-80 sorbitan laurate, sodium trideceth sulphate, PEG-150 distearate, cocamidopropylhydroxy sultaine, lauroampho-carboxy glycinate, and sodium laureth-13 carboxylate. In addition, there is included in the preferred eyelid cleanser, the polyoxyethylenesorbitan fatty acid ester PEG-80 sorbitan laurate, lauroamphocarboxy glycinate and sodium laureth-13 carboxylate. Also present in the eyelid cleanser 30 composition is PEG-15 tallow polyamine in a concentration range of 0.1–0.5% by weight. This compound is a tertiary surfactant and emollient. Sodium chloride is also present in a concentration ranging form 0.6–0.9% whereby the pH of the composition will be in the range of 8.0–8.5.

In a preferred embodiment, a preservative is included in the eyelid cleanser 30. The preferred preservative is quaternium-15. This composition is N-(3-chloroallyl) hex-amminium chloride, a quaternary ammonium salt marked by Dow Chemical Company of Midland, Mich., under the tradename Dowacil 200. Quaternium-15 is present in a concentration range of 0.1–0.5%. In the alternative, benzyl alcohol may be substituted in a concentration a concentration also of 0.1–0.5%. Finally, a chelating agent such as disodium EDTA may be used in a concentration range of 0.01–0.1%.

The eyelid cleanser 30 can be enclosed in the kit 10 in the form of a liquid solution, or alternatively, it can be in the form of a cream. Preferably, the eyelid cleanser is enclosed in a receptacle 32, 38 that is separate from the receptacle enclosing the contact lens solutions 24, 26, 28. In one embodiment as illustrated in FIG. 1, the eyelid cleanser 30 is soaked into a disposable pad 34 and wrapped within an impervious wrapper 32. One or more soaked pads 34 may be included within the kit 10 with the number of pads 34 determined by the overall size of the kit 10. FIG. 3 shows an alternative embodiment wherein the eyelid cleanser 30 is enclosed within an impervious bottle 38. In this embodiment, dry pads 52 can be enclosed for use with the bottled eyelid cleanser 38. The preferred pad 34, 52 for use with either embodiment illustrated by FIG. 1 or FIG. 3 is a lint-free pad 34. Pads 34, 52 for use with the eyelid cleanser 30 are well known in the art.

Instructions 22, 40 to explain the use of contact lens solutions 24, 26, 28 and the eyelid cleanser 30 for improved comfort while wearing lenses are included with the kit 10 of this invention. The instructions 22 can be printed in a manual included within the kit 10 as illustrated in FIG. 1 and FIG. 3 or the instructions can be printed on the housing 20, either on the outside of the housing 20 as shown in FIG. 2, or on the inside of the housing 20 (not shown) where it is not visible to the user until the kit 10 is opened. In another alternative, not shown, the instructions can be printed on each receptacle of the contact lens solutions 24, 26, 28 and eyelid cleanser 32, 38. Preferably, the instructions 22, 40 inform the contact lens wearer of the importance of use of the eyelid cleanser in conjunction with the contact lens solutions for increased comfort while wearing the contact lenses. Comfort can result from reduced irritation and ocular disease. Increased comfort can increase wearing time and result in fewer dropouts among contact lens wearers. The preferred instructions 22, 40 can inform the wearer to use the eyelid cleanser 30 prior to insertion of the lenses and following the removal of the lenses. In one preferred method of practicing this invention with the care kit for contact lens, the wearer uses the eyelid cleanser according to the instructions for removing and inserting contact lenses as provided in the kit. The user also applies the contact lens solution according to the instructions. In a more preferred method, the wearer is instructed to close the eye and gently cleanse the eyelid using horizontal or lateral side-to-side strokes. The eyelid cleanser is then rinsed off with tap water. Preferably, in the method of this invention, the instructions 22, 40 can also instruct the wearer on the proper use of the various contact lens solutions, 24, 26, 28 included in the kit. Alternatively, the use of these contact lens solutions, 24, 26, 28 can be printed on each receptacle. The instructions 22, 40 can also inform the wearer on other safety precautions regarding the insertion, removal or storage of contact lenses, washing hands before insertion or removal for example.

The foregoing description is illustrative and explanatory of preferred embodiments of the invention, and variations in the size, shape, materials and other details will become apparent to those skilled in the art. It is intended that all such variations and modifications which fall within the scope or spirit for the appended claims be embraced thereby.

What is claimed is:

1. A care kit for facilitating reduced irritation associated with wearing contact lenses, the kit comprising:

at least one solution for the care of contact lenses;

at least one non-irritating solution for cleansing eyelids;

instructions for informing contact lens wearers of the proper care of contact lenses in conjunction with eyelid hygiene for improved comfort while wearing contact lenses; and housing for securing the solution for the care of contact lenses, the solution for cleansing eyelids and the instructions wherein the non-irritating solution for cleansing eyelids comprises an anionic surfactant, a non-ionic thickener and emollient, an amphoteric surfactant, a polyoxyethylenesorbitan fatty acid ester, lauroamphocarboxy glycinate, sodium laureth-13 carboxylate, PEG15 tallow polyamine, sodium chloride, and at least one microbiological preservative.

2. The care kit of claim 1 wherein the non-irritating solution for cleansing eyelids comprises a surfactant mixture comprising PEG-80 sorbitan laurate, sodium trideceth sulphate, PEG-150 distearate, cocamidopropylhydroxy sultaine, lauroamphocarboxy glycinate, and sodium laureth-13 carboxylate, the surfactant mixture present in a concentration of 7–10%; PEG-15 tallow polyamine present in a concentration of 0.1–0.5%; sodium chloride present in a concentration of 0.6–0.9%, at least one microbiological preservative selected from the group consisting of Quaternium-15 and benzyl alcohol present in concentration of 0.1–0.5% and a chelating agent present in a concentration of 0–0.1%.

3. A care kit for facilitating reduced irritation associated with wearing contact lenses, the kit comprising:

at least one solution for the care of contact lenses;

at least one non-irritating solution for cleansing eyelids;

instructions for informing contact lens wearers of the proper care of contact lenses in conjunction with eyelid hygiene for improved comfort while wearing contact lenses; and housing for securing the solution for the care of contact lenses, the solution for cleansing eyelids and the instructions wherein the solution for cleansing eyelids is soaked into a disposable pad and enclosed within an impervious wrapper.

4. A care kit for contact lens wearers comprising: at least one component for eye care and at least one component for eyelid care, the eye care components comprising at least one contact lens solution selected from a group consisting of cleansing solution, disinfecting solution, soaking solution, wetting solution, storage solution, rinsing solution, and a combination thereof; at least one eyelid cleanser for reducing irritation or the potential for infection of eyelids, the cleanser comprising a non-irritating, antimicrobial fluid soaked into a disposable pad and enclosed within an impervious wrapper; instructions for proper use of the contact lens solution in conjunction with the eyelid cleanser for improved comfort of the wearer, and housing for securing the contact lens solution, the eyelid cleanser and the instructions.

5. A method of caring for eyes and eyelids using a care kit for contact lens wearers comprising at least one contact lens solution, at least one eyelid cleanser and instructions for use of both the contact lens solution and eyelid cleanser for improved comfort of wearer, the solution, the cleanser and the instructions secured in a housing; the method comprising:

using eyelid cleanser according to instructions for the removal and insertion of contact lenses; and applying contact lens solutions according to instructions for the removal and insertion of contact lenses wherein the eyelid cleanser comprises an anionic surfactant, a non-ionic thickener and emollient, an amphoteric surfactant, a polyoxyethylenesorbitan fatty acid ester, lauroamphocarboxy glycinate, sodium laureth-13 carboxylate, PEG-15 tallow polyamine, sodium chloride, and at least one microbiological preservative.

* * * * *